United States Patent [19]
Lo et al.

[11] Patent Number: 5,541,087
[45] Date of Patent: Jul. 30, 1996

[54] EXPRESSION AND EXPORT TECHNOLOGY OF PROTEINS AS IMMUNOFUSINS

[75] Inventors: Kin-Ming Lo, Wellesley; Yukio Sudo, Lexington; Stephen D. Gillies, Hingham, all of Mass.

[73] Assignee: Fuji ImmunoPharmaceuticals Corporation, Lexington, Mass.

[21] Appl. No.: 305,700

[22] Filed: Sep. 14, 1994

[51] Int. Cl.$^6$ .................... C07K 16/46; C12N 15/13; C12N 15/11

[52] U.S. Cl. .................... 435/697; 435/69.8; 435/70.1; 435/240.1; 435/252.3; 435/320.1; 530/387.3; 530/391.1; 530/391.7; 530/402; 530/344; 530/345; 536/23.1; 536/23.4; 536/23.53

[58] Field of Search .................... 435/69.7, 69.8, 435/70.1, 240.1, 252.3, 320.1; 530/387.3, 387.1, 391.1, 866, 867, 402, 344, 345, 391.7, 23.53, 23.1, 23.4

[56] References Cited

FOREIGN PATENT DOCUMENTS 0234592  2/1987  European Pat. Off. ........ C12N 15/00

OTHER PUBLICATIONS

Traunecker et al. [EMBO J. 10(12):3655–3659 (1991)].
Traunecker et al. [Nature 339:68–70 (1988)].
Basu et al., "Purification and Characterization of Human Recombinant IGE–Fc Fragments That Bind to the Human Affinity IgE Receptor", *Journal of Biological Chemistry*, 268:13118–13127 (1993).
Smith et al., "Single–step purification of polypeptides expressed in *Escherichia coli* as fusions with glutathione S–transferase", *Gene* 67:31–40(1988).
Gillies et al., "High–level expression of chimeric antibodies using adapted cDNA variable region cassettes", *Journal of Immunological Methods*, 125:191–202 (1989).
Gillies et al., "Antibody–targeted interleukin 2 stimulates T–cell killing of autologous tumor cells", *Proc, Natl. Acad. Sci. USA*, 89:1428–1432 (1992).
Capon et al., "Designing CD4 immunoadhesins for AIDS therapy", *Nature*, 337:525–531 (1989).
Friden et al., "Blood–Brain Barrier Penetration and in Vivo Activity of an NGF Conjugate", *Science*, 259:373–377 (1993).
Hopp et al., "A Short Polypeptide Marker Sequence Useful For Recombinant Protein Identification and Purification", *Bio/Technology*, 6:1204–1210 (1988).
Gillies et al., "Biological Activity and in Vivo Clearance of Antitumor Antibody/Cytokine Fusion Proteins", *Bioconjugate Chemistry*, 4:230–235 (1993).

*Primary Examiner*—Donald E. Adams
*Attorney, Agent, or Firm*—Testa, Hurwitz & Thibeault

[57] ABSTRACT

Disclosed are DNAs produced by recombinant techniques for inducing the expression and subsequent secretion of a target protein. The DNAs encode, in their 5' to 3' direction, a secretion cassette, including a signal sequence and an immunoglobulin Fc region, and a target protein. The DNAs can be transfected into a host cell for the expression, production and subsequent secretion of the target protein as a fusion protein. The secreted protein can be collected from the extracellular space, and further purified as desired. The secreted fusion protein additionally can be proteolytically cleaved to release the target protein from the secretion cassette.

12 Claims, 1 Drawing Sheet

EXPRESSION AND EXPORT TECHNOLOGY OF PROTEINS AS IMMUNOFUSINS

BACKGROUND

The invention relates to fusion protein expression systems for use in mammalian cells that enhance the production of a given target protein. More specifically, the invention relates to a secretion cassette, comprised of a mammalian signal peptide and a portion of mammalian immunoglobulins, which, when used as the amino-terminal fusion partner to the target protein, generally leads to high level expression and secretion of the fusion product. Such fusion proteins are useful, for example, for the production and extracellular collection of target proteins without the need for lysis of a host cell. The invention is perhaps most useful for the expression of target proteins which are not normally secreted from a host cell, are secreted at low levels from a host cell, or are toxic or otherwise deleterious to a host cell.

Expression systems employing gene fusion constructs have been used to enhance the production of proteins in bacteria. Employing a bacterial protein that is normally expressed at a very high level as the amino-terminal fusion partner of a fusion protein helps to ensure efficient transcription and translation of the message, and in some cases the secretion and solubilization of the fusion protein (Smith and Johnson (1988) Gene 67:31; Hopp et al. (1988) Biotechnology 6:1204; La Vallie et al. (1993) Biotechnology 11:187).

The major goal of expression of recombinant fusion proteins in mammalian cells has been to confer novel properties to the hybrid molecules, e.g., targeting of a cytokine or toxin in vivo, Fc receptor binding, complement fixation, protein A binding, increasing the half-life, and crossing the blood-brain barrier. Examples of recombinant fusion proteins produced in mammalian cells include cytokine immunoconjugates (Gillies et al. (1992) Proc. Natl. Acad. Sci. USA 89:1428; Gillies et al. (1993) Bioconjugate Chemistry 4:230), immunoadhesins (Capon et al. (1989) Nature 337:525), immunotoxins (Chaudhary et al. (1989) Nature 339:394), and a nerve growth factor conjugate (Friden et al. (1993) Science 259:373). Each of the foregoing publications is incorporated herein by reference. Proteins produced in mammalian cells often do not have the solubility and secretion problems encountered in bacterial expression. The use of gene fusion constructs to enhance the production or secretion of a target protein in a mammalian system has not been explored fully.

It is the object of the invention to provide DNAs which facilitate the production and secretion of a target protein. In particular, objects of the invention are to provide novel DNAs which: facilitate efficient production and secretion of hard to express proteins, such as nuclear proteins, regulatory proteins and proteins which otherwise may be toxic to a host cell, and can be adapted to any target polypeptide of interest which can be coded for and expressed in a host organism; to provide DNA constructs for the rapid and efficient production and secretion of proteins in a variety of host cells; and to provide a method for the production, secretion and collection of genetically engineered proteins, including non-native, biosynthetic, or otherwise artificial proteins, such as proteins which have been created by rational design. Other objects of the invention are to provide DNA sequences which, when fused to a polynucleotide encoding a target protein, encode a fusion polypeptide which can be purified using common reagents and techniques, and to interpose a proteolytic cleavage site between the encoded secretion cassette and the encoded target protein such that the secretion cassette can be cleaved from the target protein and the target protein can be purified independently. Still another object is to provide a procedure which is both efficient and inexpensive.

These and other objects of the invention will be apparent from the description, drawings, and claims that follow.

SUMMARY OF THE INVENTION

The present invention features a DNA of general applicability for production and secretion of fusion proteins. The DNA comprises a secretion cassette, as the amino-terminal fusion partner, and a target protein, and is termed herein an "immunofusin". The invention provides, in its various aspects, a recombinant DNA encoding the immunofusin, and methods of producing the encoded immunofusin protein. The immunofusin is a DNA which comprises a polynucleotide encoding a secretion cassette, comprising in its 5' to 3' direction a signal sequence and an immunoglobulin Fc region, and a polynucleotide encoding a target protein fused to the 3' end of the secretion cassette. A secretion cassette of the invention, once constructed, can be fused to various target proteins. Additionally, one can optimize the sequences which regulate the expression of a secretion cassette, and hence the expression of the immunofusin. The resultant DNA can be expressed at high levels in a host cell, and the fusion protein is efficiently produced and secreted from the host cell. The secreted immunofusin can be collected from the culture media without the need for lysis of the host cell, and can be assayed for activity or purified using common reagents as desired.

The portion of the DNA encoding the signal sequence preferably encodes a peptide segment which directs the secretion of the immunofusin protein and is thereafter cleaved. As used in the specification and claims, "immunoglobulin Fc region" means the carboxyl-terminal portion of an immunoglobulin heavy chain constant region. As is known, each immunoglobulin heavy chain constant region is comprised of four or five domains. The domains are named sequentially as follows: CH1-hinge-CH2—CH3(—CH4), and the Fc region of each immunoglobulin subclass lacks at least the CH1 domain. As is apparent from a review of the DNA sequences of the immunoglobulin subclasses, the DNA sequences of the heavy chain domains have cross-homology among the immunoglobulin classes, e.g., the CH2 domain of IgG is homologous to the CH2 domain of IgA and IgD, and to the CH3 domain of IgM and IgE. The portion of the DNA encoding the immunoglobulin Fc region preferably comprises at least a portion of a hinge domain, and a CH3 domain of Fcγ or the homologous domains in any of IgA, IgD, IgE, or IgM. The immunoglobulin Fc region also preferably comprises at least a portion of the DNA encoding a hinge and a CH3 domain of Fcγ or the homologous domains in any of IgA, IgD, IgE or IgM.

The currently preferred secretion cassette is a polynucleotide encoding, in its 5' to 3' direction, the signal sequence of an immunoglobulin light chain gene and the Fcγ1 region of the human immunoglobulin γ1 gene. The Fcγ1 region of the immunoglobulin γ1 gene includes at least a portion of the hinge domain and CH3 domain, or at least a portion of the hinge domain, CH2 domain and CH3 domain. The DNA encoding the secretion cassette can be in its genomic configuration or its cDNA configuration. However, the studies described below use a secretion cassette in the genomic configuration. The use of human Fcγ1 as the Fc region sequence has several advantages. For example, if the fusion protein is to be used as a biopharmaceutical, the Fcγ1 domain may confer the effector function activities to the fusion protein. The effector function activities include the biological activities such as complement fixation, antibody-directed cellular cytotoxicity, ability for placental transfer, and a longer serum half-life. The Fc domain also provides for detection by anti-Fc ELISA and purification through binding to *Staphylococcus aureus* protein A ("Protein A"). In certain applications it may be desirable to delete specific effector functions from the Fc region, such as Fc receptor binding or complement fixation.

In another embodiment the DNA sequence encodes a proteolytic cleavage site interposed between the secretion cassette and the target protein. A cleavage site provides for the proteolytic cleavage of the encoded fusion protein thus separating the Fc domain from the target protein. As used herein, "proteolytic cleavage site" is understood to mean the amino acid sequences which are cleaved by a proteolytic enzyme or other proteolytic cleavage agents. As will be described in more detail below, useful proteolytic cleavage sites include amino acids sequences which are recognized by proteolytic enzymes such as trypsin, plasmin or enterokinase K.

In another aspect, the DNA sequence of the invention is integrated within a replicable expression vector. As used herein, "vector" is understood to mean any nucleic acid comprising a nucleotide sequence of interest and competent to be incorporated into a host cell and to be recombined with and integrated into the host cell genome, or to replicate autonomously as an episome. Such vectors include linear nucleic acids, plasmids, phagemids, cosmids and the like. A preferred expression vector is pdC, in which the transcription of the immunofusin DNA is placed under the control of the enhancer and promoter of the human cytomegalovirus. The vector pdC was derived from pdEMp, which is described in Lo et al. 1991, Biochim. Biophys. Acta 1088:712 (which publication is incorporated herein by reference) as follows. The SalI-XhoI fragment containing the original enhancer and promoter sequence were replaced by the enhancer and promoter of the human cytomegalovirus by standard molecular biology techniques. The enhancer and promoter sequence of the human cytomegalovirus used was derived from nucleotides −601 to +7 of the sequence provided in Boshart et al., 1985, Cell 41:521, which is incorporated herein by reference. The vector also contains the mutant dihydrofolate reductase gene as a selection marker (Simonsen and Levinson (1983) Proc. Nat. Acad. Sci. USA 80:2495, incorporated herein by reference).

An appropriate host cell can be transformed or transfected with the DNA sequence of the invention, and utilized for the expression and secretion of a target protein. Currently preferred host cells for use in the invention include immortal hybridoma cells, myeloma cells, 293 cells, Chinese hamster ovary cells, Hela cells, and COS cells. As used herein, "gene expression" or "expression of a target protein" is understood to refer to the transcription of the DNA sequence, translation of the mRNA transcript, and secretion of the fusion protein product.

The method of the invention involves providing a DNA sequence encoding an immunofusin, transfecting the DNA sequence into a host cell by an available transfection or transformation technique, culturing the transfected host cell in a suitable media under conditions which promote the expression and secretion of the immunofusin, and collecting the fusion protein from the extracellular media. When desired, the target protein may be cleaved from the secretion cassette either before or after it is collected from the extracellular media.

Other advantages and features of the invention will be apparent from the description, drawings, and claims which follow.

BRIEF DESCRIPTION OF THE DRAWING

FIG. 1A "DNA", illustrates the DNA encoding an immunofusin protein. FIG. 1B "Fused Protein 1", illustrates the immunofusin protein prior to cleavage of the signal sequence. FIG. 1C "Fused Protein 2", illustrates the immunofusin protein after cleavage of the signal sequence. FIG. 1D "Target Protein", illustrates the target protein portion of an immunofusin protein after cleavage of the immunofusin protein at the cleavage site which is interposed between the Fc region and the target protein.

DETAILED DESCRIPTION

The present invention is a DNA comprising a polynucleotide encoding, in the 5' to 3' direction, a signal sequence, an Fc region of an immunoglobulin, and a target protein. This approach to the expression and subsequent secretion of a target protein is superior to the existing techniques because of the choice and the configuration of the secretion cassette which is placed at the 5' end of the fusion construct. Additionally, the regulatory sequences which direct the expression of the secretion cassette can be optimized, and the optimized secretion cassette can be paired with numerous target proteins, thus allowing for the efficient production of numerous fusion proteins.

The production of the immunofusin proteins is characterized as efficient and high level, because the target protein has been produced at the level of several micrograms/milliliter using the DNAs and methods according to the invention. Previously, workers in the art have rarely quantitated the expression levels of hard to express proteins due to the low levels of expression that are obtained in the known mammalian expression systems and the difficulties faced in quantitating proteins by techniques such as western blotting and RIA. Prior to the teachings of this invention, expression of microgram per milliliter of hard to express proteins would often be attempted using bacterial expression systems.

This invention is based on the concept that the ease of production and collection of a target protein could be improved if the polypeptide of interest were linked to an immunoglobulin Fc domain and the fusion protein were expressed in a host cell, in particular a complementary host cell which naturally expresses the immunoglobulin, such that the fusion protein would be readily secreted from the host cell. In addition to promoting the secretion of the fusion protein from the host cell, the Fc region can further be exploited to aid in the purification of the fused polypeptide. The general approach of the invention involves the construction of recombinant DNA which encodes a fused polypeptide, which upon expression, results in expression of an secretion cassette linked to a target protein, i.e., a protein of interest having potential or demonstrable utility.

Figure 1A:
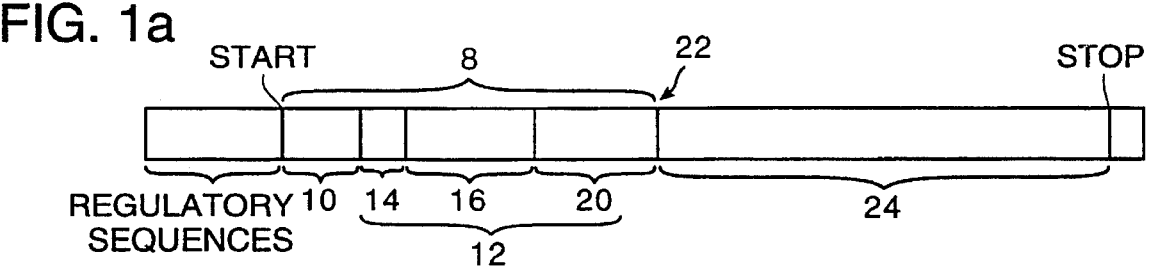
FIGS. 1A–D are a schematic illustration of an immunofusin.

The overall structure of the preferred DNA of the invention, the fusion protein it encodes, the form of the protein which is most often secreted and the target protein product after enzymatic cleavage are illustrated schematically in FIGS. 1A–D. Reference characters in the DNA FIG. 1A, are carried over into the protein, FIGS. 1B–D as corresponding primed characters. The DNA which encodes the immunofusin is shown between the start and the stop markers on the illustrated DNA sequence, FIG. 1A. Upstream regulatory elements are shown at the 5' end of the DNA and are labeled "regulatory sequences". The DNA is composed of three distinct polynucleotides which are linked together. In FIG. 1A, 3' of the regulatory sequences, which may be optimized for each secretion cassette, is a first DNA 8 which encodes a secretion cassette comprising two of the three polynucleotides: 1) a signal sequence 10, and 2) an immunoglobulin Fcγ region 12. The immunoglobulin Fcγ region is comprised of three subregions: 1) a hinge region 14, 2) a CH2 region 16, and a CH3 region 20. Attached to the 3' end of the DNA encoding the secretion cassette is the third polynucleotide, a DNA encoding the target protein 24. Optionally, DNA encoding a proteolytic cleavage site 22 can be interposed between the DNA encoding the CH3 region of the immunoglobulin Fcγ region and the DNA encoding the target protein.

Figure 1B:
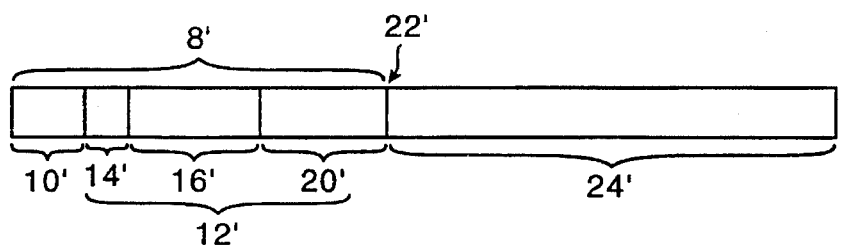
Figure 1C:
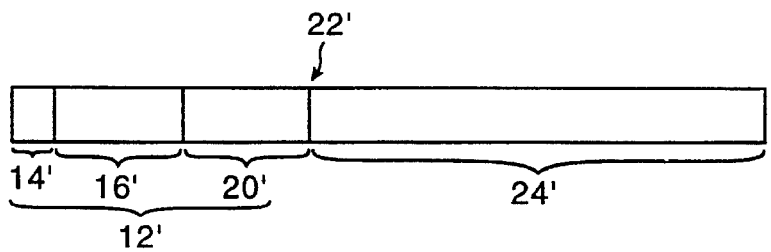
Figure 1D:
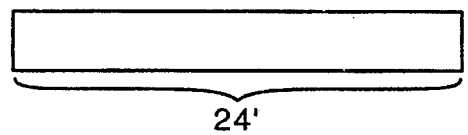

The encoded fused protein comprises the secretion cassette 8' and the target protein 24', shown as Fused Protein 1 in FIG. 1B. Most often the signal peptide 10' will be enzymatically cleaved from the fusion protein by the host cell prior to the secretion of the immunofusin, and thus Fused Protein 2, shown in FIG. 1C shows the secreted fused protein which comprises the Fcγ peptide 12' fused to the target polypeptide 24'. Both Fused Protein 1 and Fused Protein 2 show the optional interposition of a proteolytic cleavage site 22' between the CH3 domain 20' of the Fcγ region 12' and the target protein 24'. Cleavage of either Fused Protein with the appropriate proteolytic agent at the cleavage site 22' results in the release of the target protein 24' from the Fc region 12' as shown iin FIG. 1D.

The processes for manipulating, amplifying and recombining DNAs are generally well known in the art, and therefore are not described in detail herein. Methods of identifying and isolating genes encoding proteins of interest, or for constructing such genes, are well understood and developed. In general the methods involve selecting genetic material coding for amino acids which define the polypeptide of interest according to the genetic code.

Accordingly, the DNA construction principle disclosed herein can be exploited using known recombinant DNA techniques involving the use of various restriction enzymes which make sequence specific cuts in DNA to produce blunt ends or cohesive ends, DNA ligase techniques enabling enzymatic addition of sticky ends to blunt ended DNA, construction of synthetic DNAs by assembly of short oligonucleotides, cDNA synthesis techniques, polymerase chain reaction, and synthetic probes for isolating genes having a particular function. Various promoter sequences and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses. The vectors may exploit various marker genes which impart to a successfully transfected cell a detectable phenotypic property that can be used to identify which of a family of cells has successfully incorporated the recombinant DNA of the vector. Given the foregoing state of the genetic engineering art, skilled persons are enabled to practice the invention disclosed herein in view of this disclosure.

One method for obtaining the DNA encoding the various synthetic linkers disclosed herein is by assembly of synthetic oligonucleotides in a conventional, automated, polynucleotide synthesizer followed by ligation with a ligase. For example, the linkers can be synthesized as complementary DNA fragments using phosphoramidite chemistry.

The signal sequence of the invention is a polynucleotide which encodes an amino acid sequence that initiates transport of a protein across the membrane of the endoplasmic reticulum. Signal sequences which will be useful in the invention include antibody light chain signal sequences, e.g., antibody 14.18 (Gillies et.al., 1989, Jour. of Immunol. Meth., 125:191–202), antibody heavy chain signal sequences, e.g., the MOPC141 antibody heavy chain signal sequence (Sakano et al., 1980, Nature 286:5774), and any other signal sequences which are known in the art (see for example, Watson, 1984, Nucleic Acids Research 12:5145). Each of these references is incorporated herein by reference. Signal sequences have been well characterized in the art and are known typically to contain 16 to 30 amino acid residues, and may contain greater or fewer amino acid residues. A typical signal peptide consists of three regions: a basic N-terminal region, a central hydrophobic region, and a more polar C-terminal region. The central hydrophobic region contains 4 to 12 hydrophobic residues that anchor the signal peptide across the membrane lipid bilayer during transport of the nascent polypeptide. Following initiation, the signal peptide is usually cleaved within the lumen of the endoplasmic reticulum by cellular enzymes known as signal peptidases. Potential cleavage sites of the signal peptide generally follow the "(−3, −1) rule". Thus a typical signal peptide has small, neutral amino acid residues in positions −1 and −3 and lacks proline residues in this region. The signal peptidase will cleave such a signal peptide between the −1 and +1 amino acids. Thus, the portion of the DNA encoding the signal sequence may be cleaved from the amino-terminus of the immunofusin protein during secretion. This results in the secretion of a immunofusin protein consisting of the Fc region and the target protein. A detailed discussion of signal peptide sequences is provided by von Heijne (1986) Nucleic Acids Res., 14:4683 (incorporated herein by reference). As would be apparent to one of skill in the art, the suitability of a particular signal sequence for use in the secretion cassette may require some routine experimentation. Such experimentation will include determining the ability of the signal sequence to direct the secretion of an immunofusin and also a determination of the optimal configuration, genomic or cDNA, of the sequence to be used in order to achieve efficient secretion of immunofusins. Additionally, one skilled in the art is capable of creating a synthetic signal peptide following the rules presented by von Heijne, referenced above, and testing for the efficacy of such a synthetic signal sequence by routine experimentation. A signal sequence is also referred to as a "signal peptide", "leader sequence" or "leader peptides" and each of these terms having meanings synonymous to signal sequence may be used herein.

The Fc region of an immunoglobulin is the amino acid sequence for the carboxyl-terminal portion of an immunoglobulin heavy chain constant region. The Fc regions are particularly important in determining the biological functions of the immunoglobulin and these biological functions are termed effector functions. As known, the heavy chains of the immunoglobulin subclasses comprise four or five domains: IgM and IgE have five heavy chain domains, and IgA, IgD and IgG have four heavy chain domains. The Fc region of IgA, IgD and IgG is a dimer of the hinge-CH2—CH3 domains, and in IgM and IgE it is a dimer of the hinge-CH2—CH3—CH4 domains. Further the CH3 domain of IgM and IgE is structurally equivalent to the CH2 domain of IgG, and the CH4 domain of IgM and IgE is the homolog of the CH3 domain of IgG (see, W. E. Paul, ed., 1993, Fundamental Immunology, Raven Press, New York, New York, which publication is incorporated herein by reference). Any of the known Fc regions would be useful as the Fc region of the secretion cassette. However, it is important that the binding sites for certain proteins be deleted from the Fc region during the construction of the secretion cassette. For example, since coexpression with the light chain is unnecessary, the binding site for the heavy chain binding protein, Bip (Hendershot et al. (1987) Immunol. Today 8:111–114), should be deleted from the CH2 domain of the Fc region of IgE, such that this site does not interfere with the efficient secretion of the immunofusin. Likewise, the cysteine residues present in the Fc regions which are responsible for binding to the light chain of the immunoglobulin should be deleted or substituted with another amino acid, such that these cysteine residues do not interfere with the proper folding of the Fc region when it is produced as an immunofusin. In the same manner, transmembrane domain sequences, such as those present in IgM, should be deleted such that these sequences do not result in misdirecting the immunofusin to the membrane as a transmembrane protein.

Upon expression and production of the Fc region as a portion of the secretion cassette, it may retain some of the biological properties, termed "effector functions", which are native to the particular immunoglobulin class from which the Fc region is obtained. Useful effector functions include, for example, complement fixation, Fc receptor binding, binding to cell membranes, and placental transfer. In some cases, it may be advantageous to modify or remove one or more of these effector functions, such as Fc receptor binding or complement fixation, using site directed mutagenesis or other well known molecular biology techniques. For example, Duncan et al. (Nature, 1988, 332:738) have mapped the amino acids responsible for the several of the immunoglobulin gamma effector functions activities, see also, Duncan et al., 1988, 332:563; Yasmeen et al., Immunol., 1976, 116:518; Tao et al., J. Immunol., 1989, 143:2595. Each of these publications is incorporated herein by reference. The amino acids or peptide segments responsible for these function can be deleted thus removing that portion of the Fc region, or substituted with sequences which would not confer the function using well known molecular biology techniques.

The currently preferred class of immunoglobulin from which the Fc region is derived is immunoglobulin gamma-1, because it has been well characterized and is efficiently secreted from most cell types. The Fc region of the other subclasses of immunoglobulin gamma (gamma-2, gamma-3 and gamma-4) would function equally well in the secretion cassette. The Fc region of immunoglobulin gamma-1 is preferably used in the secretion cassette includes at least part of the hinge region, CH2 region, and CH3 region. In addition, the Fc region of immunoglobulin gamma-1 can be a CH2-deleted-Fc, which includes a part of a hinge region and a CH3 region wherein the CH2 region has been deleted. A CH2-deleted-Fc has been described by Gillies et al., 1990, Hum. Antibod. Hybridomas, 1:47, which publication is incorporated herein by reference.

As is apparent from the above discussion of Fc regions, the Fc regions from the other classes of immunoglobulins, IgA, IgD, IgE, and IgM, would also be useful as the Fc region of the secretion cassette. Further, deletion constructs of these Fc regions, in which one or more of the constant domains are deleted would also be useful. One of ordinary skill in the art could prepare such deletion constructs using well known molecular biology techniques.

The identity of the target protein produced in accordance with the invention is essentially unlimited. Indeed, an important feature of the invention is that it provides a generalized DNA construct, and procedure which can be adapted to facilitate recombinant production of any desired target protein. For instance, the application of the invention to the expression of the regulatory proteins, such as transcription factors which are normally localized to the nucleus, allows for the efficient secretion of such normally non-secreted proteins. In addition, regulatory proteins are in general difficult to express and the purification procedures are generally cumbersome (see, for example, Meisterernst et al. (1991) Cell 66:981). Therefore, it is especially desirable that such proteins be exported into the culture medium. Additionally, the invention can be used to enhance the production and secretion of proteins which are normally secreted at low levels. If a desired target protein includes sequences encoding a secretion signal or a transmembrane signal, these sequences can be removed from the target protein such that the secretion cassette directs the secretion of the fusion protein.

The optional proteolytic cleavage site may be any amino acid sequence which is recognized by specific cleavage agents. The specificity of cleavage agents is determined by the identity of the sequence of amino acids at or near the peptide bond which is to be hydrolyzed. A given cleavage agent may recognize the bond between two specific amino acids or may recognize a bond following one or a specific sequence of amino acids. The specificity of many cleavage agents is known. Table 1 set forth below lists various known cleavage agents and their primary (and in some cases secondary) sites of action.

TABLE 1

| Cleavage Agent | Major Site of Action | Other Sites of Action |
| --- | --- | --- |
| Trypsin | Arg, Lys | |
| Chymotrypsin | Trp, Phe, Tyr | Leu, Met, His |
| Elastase | Neutral Aliphatic Residues | |
| Pepsin | Phe, Leu, Trp | Ala, Gly, Glu |
| Papain | Arg, Lys, Gly | Wide specificity |
| Subtilisin | Aromatic and Aliphatic residues | Various |
| Thermolysin | Amino-linked bonds of Aliphatic Residues | Ala, Phe |
| S. aureus protease | Glu | Asp |
| Endoproteinase Arg C (Submaxillaris protease) | Arg | |
| Clostripain | Arg | |
| Thrombin | Arg | |
| Collagenase | X—Gly—Pro | X—Ala—Pro X—Gly—Thr |
| Lysobacter enzymogenes (endoproteinase Lys—C) | Lys | |
| Mysobacter Al-1 Protease | Lys | |
| Armillaria mellea | Lys | |
| Flavobacterium meringosepticum | Pro | |
| Factor Xa | Ile—Glu—Gly—Arg | |
| CNBr | Met | |
| BNPS-skatole | Trp | |
| N-bromosuccinimide | Trp | |
| O-iodosobenzoic acid | Trp | |
| HBr/DMSO | Trp | |
| NTCB | Cys | |
| Sodium metal in liquid ammonia | Pro | |

TABLE 1-continued

| Cleavage Agent | Major Site of Action | Other Sites of Action |
|---|---|---|
| Hydroxylamine | Asn—Gly | |
| Dilute acid | Asp—Pro | |

Other cleavage agents are known. Those preferred for use in the invention are enzymes with a primary site of action which cleave at the C-terminal side of the cleavage site residue.

The cleavage site in the fused protein generally can comprise any one or sequence of amino acids which can be cleaved by a cleavage agent specific for the site in an appropriate environment. Specificity of cleavage can be increased, and likelihood of undesired cleavage within the target protein or elsewhere in the fused polypeptide can be decreased, by selecting the cleavage agent having a site of action which is absent from the target polypeptide. The fused polypeptide is preferably cleaved under conditions in which it has assumed its native conformation. This has the effect of masking the presence of potential cleavage sites in the target polypeptide.

The invention is illustrated further by the following non-limiting examples.

EXAMPLE 1

Construction of a Secretion Cassette

The construction of an exemplary secretion cassette is described below. As would be appreciated by those of ordinary skill in the art, the signal sequence and the Fc region of an immunoglobulin could be other sequences than those described.

The signal sequence of an immunoglobulin light chain of the 14.18 antibody was selected for use as the signal sequence of the secretion cassette. The sequence of the 14.18 antibody light chain is provided in Gillies et al., 1989, Jour. Immunol. Meth., 125:191–202 and is incorporated herein by reference. The signal sequence was modified for ease of cloning as an XbaI-AflII fragment of the DNA. As would be apparent to those of skill in the art, the DNA encoding a human signal sequence could also be used. Specifically, an XbaI site was introduced 5' of the translation initiation codon and the consensus sequence for optimal ribosome binding (Kozak, 1984, Nature 308:241, incorporated herein by reference). An AflII site was introduced into the 3' end of the signal sequence by mutagenizing the DNA coding for the penultimate amino acid residue of the signal peptide from a serine to a leucine, thus the sequence ATC was mutagenized to TTA using site directed mutagenesis.

The Fc region of an immunoglobulin was selected to be the human FCγ1 genomic DNA, including the genomic configuration of the hinge, CH2 and CH3 domains. The genomic sequence of human Fcγ1 is provided in Huck et al., (1986) Nucleic Acids Res. 14:1779 and is incorporated herein by reference. As would be apparent to one of ordinary skill in the art, a CH2-deleted-Fc may also be used as the Fc region of the secretion cassette (see, Gillies et al., 1990, Hum. Antibod. Hybridomas, 1:47), in which case the CH2 domain would be deleted from the Fc region using established molecular biology techniques during the construction of the secretion cassette. The genomic DNA of FCγ1 was modified for ease of cloning as an AflII-XmaI fragment. The 5' end of the human Fc genomic DNA was mutagenized to an AflII site by performing a Polymerase Chain Reaction (PCR) using a 5' sense primer with the following sequence (Sequence ID No. 1):

GAGAATT<u>CTTAAG</u>CGAGCCCAAATCTTCTGACAAAACTCAC

This primer introduced an AflII site (underlined) and a cysteine to serine mutation (TGT to TCT, bold). The cysteine being mutated is the one that is normally involved in disulphide bonding with the light chain and thus does not affect the effector functions of the Fc region. The deletion of this cysteine may serve to enhance the production of the Fcγ1 region as the efficient production of this modified Fcγ1 region will not require the coexpression of the immunoglobulin light chain. This cysteine was also removed such that it does not interfere with the proper folding of the Fcγ1 region or the fused target protein. The 3' end of the Fcγ1 genomic DNA encodes for two XmaI restriction sites. They are located at 10 and 280 bp upstream of the translation stop codon in the CH3 domain. The distal XmaI site was destroyed by introducing a silent mutation, using site directed mutagenesis, (TCC to TCA, where the CC were the first two bases of the XmaI site) so that the XmaI site 10 bp upstream of the stop codon became unique.

The XbaI-AflII restriction fragment encoding the light chain signal peptide was then ligated to the AflII-XmaI restriction fragment encoding the Fc region. The resultant XbaI-XmaI restriction fragment therefore encodes the secretion cassette, and the gene encoding the target protein of interest can be ligated to the 3' end of the secretion cassette via the XmaI site.

In general, the DNA encoding the target protein can be ligated to the unique XmaI site through the use of a linker-adaptor, such a linker-adaptor may also include restriction endonuclease sites in addition to an XmaI site. The use of a linker-adaptor has the additional feature in that it can encode a proteolytic cleavage site for subsequent use in cleaving the target protein from the secretion cassette after production and secretion of the fusion protein. For example, the linker-adaptor can encode a lysine residue at the junction of the fusion protein, which provides the option of cleaving the target protein from the Fc domain by proteolytic enzymes such as trypsin or plasmin. Similarly, the linker adaptor can include a DNA encoding the cleavage site of enterokinase K (Asp-Asp-Asp-Asp-Lys) in order to provide for the specific cleavage of the secreted fusion protein by enterokinase K.

EXAMPLE 2

Construction of an Immunofusin

The construction of an exemplary immunofusin, including a secretion cassette and a target protein is described below. As would be apparent to those of ordinary skill in the art, other target proteins can be fused to a secretion cassette using the same or other molecular cloning techniques.

The target protein for the exemplary immunofusin was chosen to be CD26, which is a type II membrane protein having its active site within the carboxyl-terminal region of the protein which is the extracellular domain. During the construction of a CD26 immunofusin, the cytoplasmic and transmembrane domains of CD26 were deleted so that they would not interfere with the secretion of the immunofusin by the secretion cassette. The 5' end of the cDNA encoding the extracellular domain was modified for ease of cloning to include a XmaI site, which was introduced via a linker-adaptor. The 3' end of the CD26 cDNA was also modified for ease of cloning to include a XhoI site, which could be introduced downstream of the translation stop codon either by PCR or by linker-adaptor ligation.

Various linker-adaptors can be used depending upon the desire for introduction of a proteolytic cleavage site between the DNA encoding for the Fc region and the CD26 cDNA. For example, one linker-adaptor which can be used for CD26 is:

5' CCG GGT (AAA) GGC ACA GAT GAT GCT ACA G
3'          CA (TTT) TTG TGT CTA CTA CGA TGT C as provided in Sequence ID Nos. 2 and 3. The first three codons in the top strand encode the last three amino acid residues of the CH3 domain, and starting with the codon GGC is the gene sequence of the extracellular domain of CD26. This linker-adaptor had the cohesive end of an XmaI site at its 5' end and the blunt end of a PvuII site at its 3' end, the blunt ended PvuII site being a convenient site for reconstruction with the rest of the CD26 cDNA. The lysine codon (AAA, in parenthesis) in the linker-adaptor is but one of many optional amino acid sequences which are useful to provide for a proteolytic cleavage site by cleavage agents. For example, this lysine residue can be cleaved by enzymes such as trypsin or plasmin.

Alternatively, for more specific proteolytic cleavage by enterokinase K, the gene sequence encoding the enterokinase K cleavage site can be introduced via the following linker-adaptor:

5' CCG GGT TCA GGG GAT GAC GAT GAC GAT A
3'          CA AGT CCC CTA CTG CTA CTG CTA TTC GA as provided in Seq. ID Nos. 4 and 5. The nucleotides in bold encode the amino acid residues (Asp)4-Lys, which is the recognition site of enterokinase K. The linker-adaptor ends with a HindIII site, to which the CD26 gene or other target protein gene sequences can be joined.

EXAMPLE 3

Host Cells and Transfection

The preferred host cell lines include the mouse myeloma (or hybridoma) NS/0 and Sp2/0 Ag14 cells. The myeloma cells were transfected by protoplast fusion and selected in Dulbecco's modified Eagle's medium (Gibco) containing 10% fetal bovine serum and 100 nM methotrexate, as described by Gillies et al., 1989, BioTechnology, 7:799, which publication is incorporated herein by reference. Transfectants secreting the immunofusins were identified by anti-Fc ELISA, as described by Gillies et al. (1989) J. Immunol. Methods 125:191, which publication is incorporated herein by reference. The highest producers were adapted to media containing 1 µM MTX and subcloned by limiting dilutions. For the production of immunofusins, the cells were grown in Hybridoma Serum-Free Media (HSFM, Gibco) containing 1% fetal bovine serum and 1 µM MTX.

The other preferred recipient cell line is the human kidney 293 cells, which is useful for both transient and stable expression. Other cells, such as the HeLa and the Chinese hamster ovary (CHO) cells, also worked in our system. The preferred method of transfection for these adherent cells is by coprecipitation of plasmid DNA with calcium phosphate, and other methods include lipofection and electroporation.

For a description of these methods and other useful transfection methods see, Sambrook et al. (1989) *Molecular Cloning-A Laboratory Manual,* Cold Spring Harbor, N.Y., incorporated herein by reference.

EXAMPLE 4

Characterization and Purification of Immunofusins

For routine characterization by gel electrophoresis, immunofusins in the conditioned media were first captured on Protein A Sepharose (Repligen, Cambridge, Mass.) and then eluted by boiling in protein sample buffer with or without 2-mercaptoethanol. After electrophoresis on an SDS-gel, the protein bands were visualized by Coomassie staining. For example, the IL2 immunofusin, see example 5, gave a band having the molecular weight of 45 kD under reducing conditions and a band having the molecular weight of 90 kD under non-reducing conditions, showing that the IL2 immunofusin was produced as a dimer, presumably through disulphide bonding in the hinge domain of the Fc region.

For purification, the cell culture media was collected and then the immunofusins were bound on Protein A Sepharose. The immunofusins were subsequently eluted from the Protein A in a sodium citrate buffer (100 mM, pH 4). The eluate was then immediately neutralized with 0.1 volume of 1M Trishydrochloride, pH 8. In the case of CD26 immunofusin, it was shown that such an elution procedure resulted in greater than 80% recovery of the CD26 immunofusin with no loss of enzyme activity.

EXAMPLE 5

Expression of IL2 Immunofusin

The cDNA of mature IL2 protein was modified for ease of cloning to have a 5' XmaI restriction endonuclease site and a 3' XhoI restriction endonuclease site using well known molecular techniques, such as those which were as described in example 2. The sequence of the mature IL2 cDNA is provided in Taniguchi et al., 1983, Nature, 302:305 and is incorporated herein by reference. The cDNA of the mature IL2 protein was constructed using recombinant techniques as a synthetic gene in order to optimize codon usage and to introduce desirable restriction endonuclease cleavage sites. The synthetic gene was created using conventional DNA manipulation techniques. Once the synthetic IL2 cDNA was constructed, the 5' XmaI site of the IL2 cDNA was ligated to the 3' XmaI site of the secretion cassette, described in Example 1. The IL2 immunofusin, was then cloned into the expression vector pdC. The IL2 immunofusin expression vector was transfected into NS/0 and Sp2/0 as host cells by protoplast fusion, as is described by Gillies et al., 1989, Biotechnology, 7:799.

Two to three weeks after transfection, MTX-resistant NS/0 and Sp2/0 clones appeared. The initial clones were screened by anti-Fc ELISA. The IL2 immunofusin protein was collected from the media. An appropriate assay for the biological activity of IL2 was the standard T-cell proliferation assays according to Gillies et al. (Proc. Natl. Acad. Sci. (1992) 89:1428), which is incorporated herein by reference. The spent culture of the best clone contained about 100 µg/ml of IL2 immunofusin. The host cell clones which efficiently produced and secreted the IL2 immunofusin protein were subcloned in media containing 100 nM MTX, and the best subclone produced about 200 µg/ml of protein in spent culture. When MTX was left out of the media in the subcloning, the best subclone thus isolated produced about 180 μg/ml in spent culture. Thus, the construction of an IL2 immunofusin unexpectedly provided for the production of IL2 at a level which is about 80 times that which can be achieved by the expression of IL2 alone using the pdEMp vector (unpublished data), and many times of that of the IL2 that was expressed in mammalian cells (Conradt et al., 1989, J. Biol. Chem., 264:17368) and in yeast (Ernst et al., 1989, Biotechnology, 7:716). As mentioned in example 4, IL-2 immunofusin was produced as a homo-dimer of molecular weight of 90 kD, presumably through disulphide bonding in the hinge domain of the 45 kD monomers.

EXAMPLE 6

Expression of CD26 Immunofusin

The construction of CD26 as an immunofusin was undertaken to demonstrate that the invention is applicable to the expression of membrane anchored proteins such as type II membrane proteins. A type II membrane protein displays the carboxyl-terminal domain on the extracellular surface, and most often includes its active region within this carboxyl-terminal domain. The joining of a fusion polypeptide to the carboxyl-terminal region of such a protein may interfere with the proper folding of the active site, and thus reduce or prevent the production of active protein.

CD26 is a type II membrane protein comprising 766 amino acid residues. The biological function of CD26 is as a T cell activation antigen and the putative coreceptor for entry of HIV in CD4+ cells (Callebaut et al. (1993) Science 262:2045). The CD26 protein is anchored to the lipid bilayer of the plasma membrane through a hydrophobic domain between residues 7 and 28 at the N-terminus. Amino acids 1 to 6 form a short cytoplasmic tail. The rest of the protein, between residues 29 and 766, is extracellular and includes several potential N-glycosylation sites and the active site of the enzyme (Tanaka et al. (1992) J. Immunol. 149:481). The 728 carboxyl-terminal residues in CD26 protrude from the membrane surface and the C-terminus is free. A soluble CD26 expressed as an immunoadhesin, will have a conformation different from that of the native CD26, because the carboxyl-terminus in an immunoadhesin CD26 protein is not free but connected to antibody sequence. On the other hand, if we engineer an immunofusin in which the antibody sequence is amino-terminal to the target protein, such as CD26, the native conformation of CD26 will be preserved, i.e. the C-terminus is free, and the antibody sequence, herein an Fc region, takes the place of the membrane to which CD26 is normally anchored. The enzymatic and biological activities of such a soluble CD26 immunofusin will not be compromised. In addition, CD26 is a protease and its expression may be deleterious to the host cell. Thus by efficiently exporting the CD26 protease outside of the host cell in the form of an immunofusin, a higher level of expression can be achieved.

A 2.3 kb cDNA fragment encoding the extracellular domain of CD26 was used to construct the CD26 immunofusin expression vector. The DNA sequence of CD26 is provided in Tanaka et al., 1992, J. Immunol., 149:481 and is incorporated herein by reference. CD26 was fused 3' of the secretion cassette as described above in example 2, and then the secretion cassette and CD26 target protein were cloned into the expression vector pdC using the XbaI restriction endonuclease site 5' of the light chain signal sequence and the XhoI restriction endonuclease site 3' of the CD26 protein as described in example 2 above. The resultant CD26 immunofusin expression vector was transfected into a host cell as described in Example 3 above. MTX-resistant clones from transfected NS/0 and Sp2/0 cells were screened by anti-Fc ELISA and DPPIV activity assay. CD26 is also known as DPPIV, which is an exopeptidase that cleaves after amino-terminal X-P (X can be any amino acid residue, and P is proline). DPPIV enzyme activity of the CD26 immunofusin was assayed according to Tanaka et al., Proc. Natl. Acad. Sci., 1993, 90:4586, incorporated herein by reference, using glycylproline p-nitroanilide tosylate (Gly-Pro-pNA) as a substrate. The best NS/0 clone produced about 3.5 μg/ml of CD26 immunofusin. The DPPIV moiety of the protein product was determined to be fully active, having $K_M$ and $k_{cat}$ values similar to those of the native CD26. Furthermore the enzymatic activity of CD26 immunofusin was inhibited by known peptide inhibitors in a dose-dependent manner. The peptide inhibitors tested included the tripeptides IPI and VPL and APL, each of which inhibited the CD26 enzyme activity greater than 30% at 0.15 mM, greater than 70% at 1 mM and greater than 90% at 4 mM. As a control known non-inhibitor peptides were also tested for their effect upon CD26 enzyme activity and the known non-inhibitors, GGG and GPHyP (wherein HyP is hydroxproline), were found to have no effect on the CD26 activity when incubated with the CD26 immunofusin at concentrations ranging between 0.01 mM and 11 mM.

EXAMPLE 7

Expression of Tat Immunofusin

The invention was also applied to the expression of regulatory proteins which are normally localized to the nucleus. Because regulatory proteins are in general difficult to express and purify, it is especially desirable to devise a method by which such proteins can be efficiently secreted from a host cell. Immunofusin constructs of Tat and Rev (described in example 8), which are two proteins encoded by the human immunodeficiency virus (HIV) that regulate expression of viral proteins in the cell nucleus, were made in order to determine the efficiency with which these proteins can be expressed and collected. We obtained high level expression and secretion of the Tat and Rev immunofusins, and readily purified the immunofusins in a single step.

A 260 base-pair cDNA fragment encoding Tat was cloned into the XmaI and XhoI sites of the pdC expression vector by modification of the 5' and 3' ends of the Tat protein using recombinant DNA techniques as described above. The sequence of the cDNA encoding the Tat protein is provided in Ratner et al., 1985, Nature, 313:277, and is incorporated herein by reference. Specifically, the sequence at the 5' end was modified to, Seq. ID No. 6, <u>C CCG GGT</u> CGC ATG GAG . . . , where the underlined sequence is the XmaI site and the ATG in bold is the translation start codon of the Tat gene. At the 3' end, an XhoI site was introduced immediately downstream of the translation stop codon by standard PCR techniques. The Tat immunofusin expression vector was then transfected into a host cell, as described above, and the host cells were analyzed for production of Tat immunofusin protein. High level expression was obtained in transiently transfected 293 cells and stably transfected NS/0 cells. Stable NS/0 clones produced about 3 μg/ml of a 48 kD protein, analyzed on a SDS-gel under reducing conditions. This protein was confirmed to be Tat immunofusin by an anti-Tat antibody (Cat. #7001, American BioTechnologies, Cambridge, Mass.).

The Tat immunofusin was shown to be active by the following transient expression experiment in 293 cells, the results of which are presented below in Table 2. The expression vector for Tat immunofusin was cotransfected with a separate vector containing LTR-TAR-Kappa, where LTR-TAR is the long terminal repeat DNA sequence of HIV that is transactivated by the Tat protein, and Kappa is the gene sequence encoding the Kappa light chain of immunoglobulin. To measure expression levels of Fc-Tat (Tat immunofusin) and Kappa, the supernatants were assayed by anti-Fc and anti-Kappa ELISA respectively. In Table 2, pdC-Fc-Tat represents the pdC expression vector for Tat immunofusin; LTR-TAR-Kappa represents the expression vector for Kappa light chain, in which the LTR-TAR regulatory region can be transactivated by Tat; and pCEP-Tat is an expression vector for Tat, whose transcription is under the control of the human cytomegalovirus enhancer and promoter. pCEP-Tat was used as a positive control to monitor the transactivation of the LTR-TAR-Kappa by Tat protein. As a negative control LTR-TAR-Kappa was transfected alone to demonstrate that it is not transactivated in the absence of Tat protein or Tat immunofusin. As shown in Table 2, high level expression of the Tat immunofusin was observed in transfection 1; high level expression of both Tat and Kappa light chain were observed in the cotransfection experiment, transfection 2. Transactivation of Kappa by Tat was seen in the positive control, transfection 3, as expected. Little or no expression of Kappa was seen in the negative control, transfection 4, also as expected. Therefore, the Kappa light chain is expressed only through transactivation of the LTR-TAR region by a functional Tat protein, and the Tat immunofusin provides a functional Tat protein which is readily secreted from the host cell. This result also demonstrates that the secretion cassette is able to direct the secretion of a protein which is normally transported to the nucleus of the host cell.

TABLE 2

| DNA used in transfection | ELISA (ng/ml) | |
|---|---|---|
| | Fc | Kappa |
| 1.) pdC-Fc-Tat | >3000 | 0 |
| 2.) pdC-Fc-Tat, LTR-TAR-Kappa | 1600 | 160 |
| 3.) PCEP-Tat, LTR-TAR-Kappa | 0 | 277 |
| 4.) LTR-TAR-Kappa | 0 | 3 |

EXAMPLE 8

Expression of Rev Immunofusin

A 350 base-pair cDNA fragment encoding Rev was modified to include a 5' XmaI site and a 3' XhoI site and then ligated 3' of the described secretion cassette in the pdC expression vector. The sequence of the cDNA encoding the Rev protein is provided in Ratner et al., 1985, Nature, 313:277, and is incorporated herein by reference. Specifically, the 5' end of the cDNA was modified to C CCG GGT CGC ATG GCA ... (Seq. ID No. 7), where the underlined sequence is the XmaI site and the ATG in bold is the translation start codon of the Rev gene. At the 3' end, an XhoI site was introduced immediately downstream of the translation stop codon by standard PCR techniques. High level expression was obtained in transiently transfected 293 cells and stably transfected NS/0 cells. Stable NS/0 clones produced about 3 μg/10⁶ cells/day of the Rev immunofusin, which has a molecular weight of about 50 kD when analyzed on a SDS-gel under reducing conditions.

EXAMPLE 9

Site-specific Proteolytic Cleavage of an Immunofusin

An exemplary cleavage of an immunofusin is described below, as would be apparent to one of ordinary skill in the art, each of the above described immunofusins could be cleaved from their respective secretion cassettes using the same method or an analogous method.

A CD26 immunofusin having a lysine residue ("Fc(Lys)-CD26 immunofusin"), introduced by linker adaptor during construction of the immunofusin between the Fc region and the CD26 target protein sequence was cleaved using trypsin. To cleave the Fc(Lys)-CD26 immunofusin, the immunofusin was bound on Protein A Sepharose and cleaved at the desired lysine position by trypsin to release CD26 as follows: Fc(Lys)-CD26 immunofusin bound on Protein A Sepharose was incubated with a 1% trypsin solution at 37° C. for 2 hr. Trypsin inhibitor (Sigma) was then added to stop any further digestion. The supernatant was then removed and analyzed on an SDS-gel under reducing conditions. After Coomassie staining, a band having a molecular weight of 110 kD, which corresponds to the size of CD26 without the secretion cassette, was obtained. As a control, CD26 immunofusin, without the lysine residue at the junction of the fusion between the Fc domain and the CD26 target protein ("Fc-CD26 immunofusin"), was bound on Protein A Sepharose and similarly treated. The CD26 was found to not be released from the secretion cassette of the Fc-CD26 immunofusin, as was expected, and this also confirmed the specific cleavage of the immunofusin at the amino acid lysine which was inserted between the CH3 domain of the Fc region and the target CD26 protein. As a further control, an identical aliquot of Fc-CD26 immunofusin which was bound to Protein A Sepharose was boiled in the protein sample buffer and SDS-gel analysis of the supernatant showed a 140 kD band corresponding to the full length CD26 immunofusin protein monomer.

The results from the gel electrophoresis experiment were confirmed by DPPIV activity assays of the tryptic digests. Quantitative recovery of the DPPIV enzymatic activity was obtained in the supernatant when the Fc(Lys)-CD26 immunofusin bound to Protein A Sepharose was treated with trypsin. In the parallel experiment with Fc-CD26 immunofusin, there was no DPPIV activity in the supernatant, because the CD26 protein was not released from the Protein A Sepharose.

EXAMPLE 10

Expression of OSF-2 Immunofusin

OSF-2 is a 80-kD secretory protein that is involved in the ossification process. The sequence the DNA encoding OSF-2 is provided in Takeshita et al., 1993, Biochem. J. 294:271, and is incorporated herein by reference. The cDNA encoding the OSF-2 protein with its signal peptide was cloned into the expression vector pdC. NS/0 cells were used for stable transfection and 293 cells were used for transient expression; but in neither case was the OSF-2 protein detected.

The OSF-2 cDNA was then adapted to be expressed as an immunofusin. At the 3' end, the XbaI site at the translation stop codon was converted to an XhoI site by linker ligation. At the 5' end the following linker-adaptor was used:

5' <u>CCG GGT</u> AAA AAC AAT CAT TAT GAC AA
3'         <u>CA</u> TTT TTG TTA GTA ATA CTG TTC TAG as provided in Seq. ID Nos. 8 and 9. The nucleotides in bold encode the N-terminus of the mature OSF-2 protein, ending with BglII cohesive ends. These BglII cohesive ends were ligated to the BglII-XhoI fragment of the OSF-2 cDNA. The XmaI cohesive ends at the 5' end of the linker-adaptor (underlined) were ligated to the unique XmaI site in the immunofusin expression vector.

High level expression was obtained in transiently transfected 293 cells and stably transfected NS/0 cells. Stable NS/0 clones produced about 5 to 7 µg/ml of a 110 kD protein, when analyzed on a SDS-gel under reducing conditions. This protein was confirmed to be the OSF-2 immunofusin by Western blotting with an anti-OSF-2 antibody.

It was also found that the expression of OSF-2 as an immunofusin in a mammalian system was superior to the expression of OSF-2 in the thioredoxin gene fusion expression system in *E. coli* (LaVallie et al., 1993, Biotechnology, 11:187). The thioredoxin gene fusion system was designed to circumvent the formation of inclusion bodies because fusion to thioredoxin increases the solubility of many heterologous proteins produced in the *E. coli* cytoplasm. To test this system for the expression of OSF-2, the cDNA encoding the mature OSF-2 was inserted into the SmaI site of the pTrxFus vector (Invitrogen, San Diego, Calif.), thus creating a thioredoxin OSF-2 fusion protein. The supplier's protocol for the expression of the fusion proteins was followed. The thioredoxin OSF-2 fusion protein was expressed, and, as a control, the thioredoxin protein was expressed alone without a fusion partner. The results showed that although thioredoxin alone could be produced as a soluble protein at a high level, the thioredoxin OSF-2 fusion protein was present only in the insoluble fraction. Therefore, in addition to the lack of post-translational modification in bacterial expression, a relatively complex mammalian protein such as OSF-2 was not synthesized as a soluble protein when fused to thioredoxin.

EXAMPLE 11

Expression of βIG-H3 Immunofusin

βIG-H3, a gene product which is induced by transforming growth factor-β, is a 68-kD secretory protein that shares sequence homology with OSF-2. The sequence of cDNA encoding βIG-H3 is provided in Skonier et al. (1992) DNA and Cell Biology, 11:511, and is incorporated herein by reference. The cDNA encoding the native βIG-H3 was cloned into the expression vector pdC; but attempts to obtain stable transfectants producing βIG-H3 were unsuccessful.

The βIG-H3 cDNA was then adapted to be expressed as an immunofusin. At the 3' end, the BsmI site downstream of the translation stop codon was converted to an XhoI site by linker ligation. At the 5' end, the following linker-adaptor was used:

5' CCG GGT AAA GCC CTG GGC C
3'         CA TTT CGC GAC (Seq. ID. Nos. 10 and 11). The nucleotides in bold encode the N-terminus of the mature βIG-H3 protein. The linker-adaptor had XmaI cohesive ends for ligating to the expression vector as described in the above examples, and ApaI cohesive ends for ligating to the ApaI site at the 5' end of the cDNA Sequence encoding the mature βIG-H3.

High level expression was obtained in transiently transfected 293 cells and stably transfected NS/0 cells. Stable NS/0 clones produced about 3.5 µg/10$^6$ cells/day of a 100 kD protein when analyzed on a SDS-gel under reducing conditions. This protein was confirmed to be the βIG-H3 immunofusin by Western blotting with anti-βIG-H3 antibody.

EXAMPLE 12

Expression of the Soluble Form of IgE Receptor as an Immunofusin

The high affinity IgE receptor alpha subunit (IgE-R), the DNA sequence of which can be found in Kochan et al. (1988) Nucleic Acids Res. 16:3584 and is incorporated herein by reference, was constructed as an immunofusin as follows: An XmaI site was introduced to the 5' end of the cDNA encoding the mature IgE-R so that the sequence at the junction of the fusion was <u>CCCG GGT</u> GTC CCT CAG - - - (Seq. ID No. 12), where the XmaI site is underlined and the three codons in bold are the first three amino acid residues of the mature IgE-R. At the 3' end of the IgE-R, the cDNA encoding the transmembrane domain and the rest of the C-terminus was deleted and a translation stop codon was placed after the last codon of the extracellular domain. The sequence of the IgE-R immunofusin at the 3' end was thus TAC TGG CTA TAA <u>CTC GAG</u> (Seq. ID No. 13), where the three codons in bold were the last three amino acid residues of the extracellular domain of the IgE-R, and they were followed by a stop codon and an XhoI site (underlined).

The pdC expression vector containing the IgE-R immunofusin was transfected into 293 cells and NS/0 cells. High levels of expression (3 to 5 µg/ml) of the IgE-R immunofusin were detected in the cell culture media by anti(Fc) ELISA. SDS-gel analysis under reducing conditions showed a band of the expected size of 70 kD. The partially purified protein (on Protein A Sepharose) was shown to bind IgE in an IgE-R/IgE ELISA.

EXAMPLE 13

Expression of Fcγ1

Fcγ1 was expressed by itself without a C-terminal target protein. This was achieved by ligating the following linker (having XmaI and xhoI cohesive ends)

5' CCG GGT AAA TAG C
3'         CA TTT ATC GAG CT (Seq. ID Nos. 14 and 15), to the XmaI and XhoI sites of the pdC to reconstruct the coding region of Fc. High levels of expression was detected by anti(Fc) ELISA in the cell culture media of the transiently transfected 293 cells (5 to 7 µg/ml) and stably transfected NS/0 clones (5 to 10 µg/ml). SDS-gel analysis under reducing conditions showed an Fc band of the expected size of 31 kD.

OTHER EMBODIMENTS

The invention may be embodied in other specific forms without departing from the spirit or essential characteristics thereof. The present embodiments are therefore to be considered in all respects as illustrative and non-restrictive, the scope of the invention being indicated by the appended claims rather than by the foregoing description, and all changes which come within the meaning and range of equivalency of the claims are therefore intended to be embraced therein.

---

What is claimed is:

1. A DNA encoding a fusion protein comprising a polynucleotide encoding, from its 5' to 3' direction:
   a) a signal sequence;
   b) an immunoglobulin Fc region which lacks at least the CH1 domain; and
   c) a target protein sequence.

2. The DNA of claim 1 wherein the signal sequence encodes a signal peptide which directs secretion of the fusion protein and is then removed by enzymatic cleavage.

3. The DNA of claim 1 wherein the Fc region is altered to delete at least one effector function activity.

4. The DNA of claim 1 wherein the Fc region comprises a hinge, a CH2 domain and a CH3 domain of immunoglobulin gamma.

5. The DNA of claim 1 wherein the Fc region comprises a hinge region and a CH3 domain of immunoglobulin gamma.

6. The DNA of claim 1 further comprising a polynucleotide encoding a proteolytic cleavage site interposed 3' of said polynucleotide encoding said immunoglobulin Fc region and 5' of said polynucleotide encoding said target protein.

7. A replicable expression vector for transfecting a mammalian cell, said vector comprising the DNA of claim 1.

8. A host cell which expresses the DNA of claim 1.

9. A method of producing a fusion protein comprising the steps of:
   1) culturing the host cell of claim 8 in a medium under conditions to promote expression and secretion of said fusion protein; and
   2) collecting the fusion protein from the medium.

10. The method of claim 9 wherein the fusion protein has bioactivity of the target protein.

11. The method of claim 9 further comprising the additional steps, after step 2, of:
   3) cleaving the Fc region from the target protein; and
   4) collecting the target protein.

12. A method of producing a fusion protein comprising the steps of:
   1) culturing the host cell of claim 8 in a medium under conditions to promote expression and secretion of said fusion protein;
   2) cleaving the Fc region from the fusion protein; and
   3) collecting the target protein.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GAGAATTCTT AAGCGAGCCC AAATCTTCTG ACAAAACTCA C                     41

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

CCGGGTAAAG GCACAGATGA TGCTACAG                     28

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CTGTAGCATC ATCTGTGTTT TTAC                     24

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

CCGGGTTCAG GGGATGACGA TGACGATA                     28

( 2 ) INFORMATION FOR SEQ ID NO:5:

( i ) SEQUENCE CHARACTERISTICS:
        ( A ) LENGTH: 28 base pairs
        ( B ) TYPE: nucleic acid

```
          ( C ) STRANDEDNESS: single
          ( D ) TOPOLOGY: linear ( i i ) MOLECULE TYPE: cDNA ( x i ) SEQUENCE DESCRIPTION: SEQ ID NO:5:

AGCTTATCGT CATCGTCATC CCCTGAAC                                    28

( 2 ) INFORMATION FOR SEQ ID NO:6:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:6:

CCCGGGTCGC ATGGAG                                                 16

( 2 ) INFORMATION FOR SEQ ID NO:7:

( i ) SEQUENCE CHARACTERISTICS:
                ( A ) LENGTH: 16 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:7:

CCCGGGTCGC ATGGCA                                                 16

( 2 ) INFORMATION FOR SEQ ID NO:8:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:8:

CCGGGTAAAA ACAATCATTA TGACAA                                      26

( 2 ) INFORMATION FOR SEQ ID NO:9:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: cDNA ( x i ) SEQUENCE DESCRIPTION: SEQ ID NO:9:

GATCTTGTCA TAATGATTGT TTTTAC                                      26

( 2 ) INFORMATION FOR SEQ ID NO:10:

( i ) SEQUENCE CHARACTERISTICS:
                ( A ) LENGTH: 19 base pairs
                ( B ) TYPE: nucleic acid
                ( C ) STRANDEDNESS: single
                ( D ) TOPOLOGY: linear ( i i ) MOLECULE TYPE: cDNA
```

( x i ) SEQUENCE DESCRIPTION: SEQ ID NO:10:

CCGGGTAAAG CCCTGGGCC 19

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

CAGGGCTTTA C 11

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

CCCGGGTGTC CCTCAG 16

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

TACTGGCTAT AACTCGAG 18

( 2 ) INFORMATION FOR SEQ ID NO:14:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

CCGGGTAAAT AGC 13

( 2 ) INFORMATION FOR SEQ ID NO:15:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

TCGAGCTATT TAC 13